US008110702B2

(12) United States Patent
Huang et al.

(10) Patent No.: US 8,110,702 B2
(45) Date of Patent: *Feb. 7, 2012

(54) PROCESS FOR THE MANUFACTURE OF SUBSTITUTED 2-CYANO CINNAMIC ESTERS

(75) Inventors: Jing Huang, Shanghai (CN); Shuping Jing, Shanghai (CN); Reinhard Karge, Staufen (DE); Ralf Proplesch, Gipf-Oberfrick (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/889,896

(22) Filed: Sep. 24, 2010

(65) Prior Publication Data
US 2011/0014140 A1    Jan. 20, 2011

Related U.S. Application Data

(62) Division of application No. 12/523,771, filed as application No. PCT/EP2008/000372 on Jan. 18, 2008, now Pat. No. 7,985,870.

(30) Foreign Application Priority Data

Jan. 26, 2007  (EP) ..................................... 07001781
Feb. 8, 2007   (CN) .......................... 2007 1 0007571

(51) Int. Cl.
*C07C 69/76* (2006.01)

(52) U.S. Cl. ....................................... 560/101; 560/103
(58) Field of Classification Search .................. None
See application file for complete search history.

(56) References Cited

U.S. PATENT DOCUMENTS

| 5,347,032 A | 9/1994 | Reichelt et al. |
| 5,451,694 A | 9/1995 | Kuhn et al. |
| 6,271,410 B1 | 8/2001 | John et al. |

FOREIGN PATENT DOCUMENTS

| EP | 430023 | 6/1991 |
| WO | 96/38409 | 12/1996 |
| WO | WO 99/11261 | 3/1999 |

OTHER PUBLICATIONS

Cragoe et al. JOC (1950), 15, 381-390.*
International Search Report for PCT/EP2008/000372, mailed Apr. 23, 2008.
Written Opinion of the International Searching Authority for PCT/EP2008/000372, mailed Apr. 23, 2008.

* cited by examiner

*Primary Examiner* — Kamal Saeed
*Assistant Examiner* — Nyeemah A Grazier
(74) *Attorney, Agent, or Firm* — Nixon & Vanderhye P.C.

(57) ABSTRACT

The invention relates to an improved process for the manufacture of substitute 2-cyanocinnamic esters. This novel economical process provides products in high purity and yields.

9 Claims, No Drawings

PROCESS FOR THE MANUFACTURE OF SUBSTITUTED 2-CYANO CINNAMIC ESTERS

This application is a divisional of commonly owned copending U.S. application Ser. No. 12/523,771, filed on Jul. 20, 2009, which is the national phase application under 35 USC §371 of PCT/EP2008/000372, filed Jan. 18, 2008 which designated the US and claims benefit of EP 07001781.9, filed Jan. 26, 2007 and Chinese Application No. 200710007571.8, filed Feb. 8, 2007 the entire contents of each of which are hereby incorporated by reference.

This invention relates to an improved process for the manufacture of substituted 2-cyanocinnamic esters. This novel economical process provides products in high purity and yields.

Substituted 2-cyanocinnamic esters such as 2-cyano-3,3-diarylacrylic esters are highly effective UV-absorbers which are, for example, used as light stabilizers in plastics or as sunscreening agents in cosmetic products.

Substituted 2-cyanocinnamic esters may be prepared by Knoevenagel condensation of cyanoacetic esters and carbonyl compounds as e.g. disclosed in EP430 023, U.S. Pat. No. 2,623,060, U.S. Pat. No. 4,178,303 or JP 1293 982. The catalyst is preferably a mixture of glacial acetic acid and ammonium acetate, the reaction water formed being removed as an azeotrope with an organic solvent such as cyclohexane, hexane, heptane, benzene, toluene or xylene. However, for the achievement of high yields, the processes of the prior art require long reaction times, which favor the formation of unwanted by-products.

U.S. Pat. No. 5,451,694 discloses the use of $C_3$-$C_6$ monocarboxylic acids in the presence of ammonium ions in the absence of organic solvents in order to reduce the reaction time to about 5 h while achieving good yields. However, based on the molar ratio of cyanoacetate ester to carbonyl compound employed this process yields either a low conversion based on the carbonyl compound or a low conversion based on the cyanoacetate ester.

Thus, the object of the invention was to provide an economical process for the manufacture of substituted 2-cyanocinnamic esters having reduced reaction times compared to the prior art process despite using an organic solvent and giving good yields based on the carbonyl compound as well as on the cyanoacetate ester.

It has now surprisingly been found that this object can be achieved by the use of a specific molar ratio the cyanoacetate ester to the carbonyl compound using a $C_3$-$C_6$ monocarboxylic acid in the presence of ammonium ions and in the presence of an organic solvent. Furthermore, it has been found that the amount of catalyst, i.e. ammonium ions is critical for the conversion.

Thus, in a first embodiment, the invention relates to a process for the manufacture of substituted 2-cyanocinnamic esters of formula I

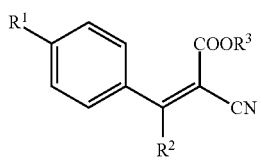

wherein
$R^1$ is hydrogen, $C_1$-$C_4$ alkyl groups, $C_1$-$C_4$ alkoxy group
$R^2$ is hydrogen, $C_1$-$C_4$ alkyl or phenyl and
$R^3$ is a $C_1$-$C_{12}$ alkyl, wherein a cyanoacetic ester of the formula II is reacted with a carbonyl compound of formula III

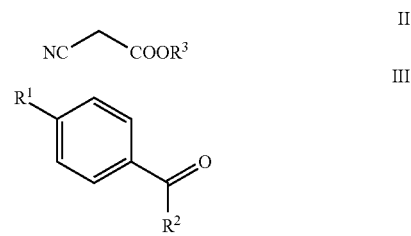

in the presence of
 (i) an organic solvent,
 (ii) a $C_3$-$C_6$ monocarboxylic acid and
 (iii) an ammonium compound
with the proviso that the molar ratio of the cyanoacetic ester of the formula II to the carbonyl compound of formula III is in a range of about 0.65 to 0.9, preferably in the range of 0.7 to 0.8, even more preferably about 0.7.

In a further embodiment, the invention relates to a process as described above wherein the molar ratio of the ammonium compound to the carbonyl compound is selected to be in the range of about of 0.6 to 1.5, preferably in the range of about 0.7 to 1.3, even more preferably in the range of about 0.7 to 1.2 such as e.g. in the range of 0.7 to 0.85 (single addition) or in the range of about 1.0 to 1.2 (stepwise addition).

In a particular preferred embodiment the invention relates to a process for the manufacture of 2-ethylhexyl 2-cyano-3,3-diphenylacrylate (INCI: octocrylene), wherein 2-ethylhexyl cyanoacetate is reacted with benzophenone in the presence of
 (i) an organic solvent,
 (ii) a $C_3$-$C_6$ monocarboxylic acid and
 (iii) an ammonium compound
with the proviso that the molar ratio of 2-ethylhexyl cyanoacetate to benzophenone is in the range of about 0.65 to 0.9, preferably in the range of about 0.7 to 0.8, even more preferably in the range of about 0.7. In an even more preferred embodiment, the molar ratio of the ammonium compound to the carbonyl compound is selected to be in the range of about of 0.6 to 1.5, preferably in the range of about 0.7 to 1.3, even more preferably in the range of about 0.7 to 1.2 such as e.g. in the range of 0.7 to 0.85 (single addition) or in the range of about 1.0 to 1.2 (stepwise addition).

In all embodiments of the invention preferred cyanoacetic esters II include, for example, methyl cyanoacetate, ethyl cyanoacetate, isoamyl cyanoacetate and 2-ethylhexyl cyanoacetate, in particular 2-ethylhexyl cyanoacetate.

In all embodiments of the invention preferred carbonyl compounds III include, for example, benzaldehyde, anisaldehyd and benzophenone, in particular benzophenone.

In all embodiments of the invention preferred $C_3$-$C_6$ monocarboxylic acids include, for example, propionic acid, n-butyric acid, iso-butyric acid, n-valeric acid, iso-valeric acid and n-caproic acid, in particular n-propionic acid. The amount of the monocarboxylic acid used is not critical and can vary from 0.1 to 10, preferably from 0.5 to 3.5 mol, per mol of cyanoacetic ester II.

In all embodiments of the invention, the ammonium compound include compounds capable of forming ammonia ions such as ammonia and ammonium salts. Preferably ammonium salts of monocarboxylic acids, such as ammonium acetate, ammonium benzoate or ammonium formate are used in the process according to the invention, most preferably ammonium acetate or ammonium benzoate, in particular ammonium acetate. In case ammonia is used for the generation of ammonium ions, it can, for example, be used in the form of an aqueous solution or it may be introduced via addition of gaseous ammonia to the solvent/acid medium of the reaction or via dewatering of aqueous solutions of ammonia in the solvent/acid medium. Thus, the invention also relates to a process according to the invention, wherein an ammonium salt is formed via addition of ammonia to the corresponding $C_3$-$C_6$ monocarboxylic acid used in the reaction.

In all embodiments of the invention the organic solvent is preferably chosen from aliphatic solvents or aromatic solvents or mixtures thereof, most preferably from aliphatic solvents. The term aliphatic solvent includes aliphatic or alicyclic hydrocarbon solvents which may be linear or branched and/or optionally substituted such as for example pentane, hexane, cyclohexane, heptane, octane, isooctane, methyl cyclohexane or dekalin or mixtures thereof. The term aromatic solvent includes solvents such as benzene, toluene, xylene or tetralin or mixtures thereof. In all embodiments of the invention preferably an aliphatic solvent is used (or mixtures thereof), even more preferably hexane, cyclohexane, heptane, isooctane or methyl cyclohexane or mixtures thereof and in particular heptane or cyclohexane or mixtures thereof.

In all processes for the manufacture of substituted 2-cyanocinnamic esters according to the invention the reaction temperature may vary from about 70° C. to 130° C. Preferably, the reaction temperature ranges from about 90° C. to 120° C. Preferably, the temperature is chosen in order to maintain the reaction at reflux. The reaction may be conducted above atmospheric pressure or under partial vacuum in order to achieve the desired temperature condition. The monocarboxylic acid/solvent/water mixture can be distilled off at atmospheric pressure or at reduced pressure, for example from about 20 to 400 mbar e.g. using a Dean-Stark water separator. As soon as no more water separates out, the reaction can be regarded as being terminated. This is generally the case after from about 3 to 8 hours. The reaction product is worked up in a usual manner by separating the organic and the aqueous phase, optionally washed and finally distilled for further purification. The non converted starting materials such as the carbonyl compound and/or the cyanoacetate ester as well as the solvent and the $C_3$-$C_6$ monocarboxylic acid can be recycled by conventional methods such as via distillation or crystallization. Preferred processes according to the invention include the recycling of unreacted starting materials.

Surprisingly it has been found that keeping the reaction temperature below 100° C., in particular at about 95° C. (while maintaining the reaction at reflux by adjusting the pressure) significantly reduced the formation of the corresponding 2-cyano-3,3-diphenyl-2-propenamide derivative. This is important as the amide derivative exhibits a similar boiling point and can not be easily removed by distillation from the substituted 2-cyanocinnamic esters. Thus, in all processes for the manufacture of substituted 2-cyanocinnamic esters according to the invention the reaction temperature is preferably maintained below 100° C. by applying partial vacuum in order to maintain the reaction at reflux. Thus, the invention also relates to a processes for the manufacture of substituted 2-cyanocinnamic esters according to the invention wherein the reaction temperature is selected in the range of about 90-100° C., in particular at about 95° C. and the pressure is selected such as to maintain the reaction at reflux. Furthermore, it has been found, that if the temperature is kept below 100° C. it is advantageous to add the ammonium compound not all at once, but charge it stepwise to the reaction. Preferably an initial dose of the ammonium compound in the range of 2 to 3 times (in grams) of the consecutive dosages is added to the reaction followed by several (e.g. 1, 2, 3, 4, 5, 6, 7, 8, 9 or 10 dosages) consecutive dosages over a certain period of time such as e.g. 1 portion per hour for 5 times. If the ammonium compound is added stepwise, preferably the molar ratio of the ammonium compound to the carbonyl compound is selected to be in the range of about 0.9 to 1.3, more preferably in the range of about 1.0 to 1.2 such as e.g. of about 1.1

In another embodiment, the invention relates to a composition comprising a substituted 2-cyanocinnamic esters of formula I

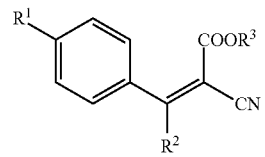

wherein
$R^1$ is hydrogen, $C_1$-$C_4$ alkyl groups, $C_1$-$C_4$ alkoxy group
$R^2$ is hydrogen, $C_1$-$C_4$ alkyl or phenyl and
$R^3$ is a $C_1$-$C_{12}$ alkyl and about 0.01 to 0.5 wt.-%, preferably about 0.05 to 0.4 wt.-%, in particular about 0.1 to 0.38 wt.-% of the corresponding 2-cyano-3,3-diphenyl-2-propenamide derivative. The amount of the substituted 2-cyanocinnamic esters of formula I in the composition according to the invention is preferably in the range of about 97 to 99.99 wt.-%, more preferably in the range of about 99 to 99.50 wt.-%. In particular, the invention relates to a composition according to the invention wherein the substituted 2-cyanocinnamic esters of formula I is 2-ethylhexyl 2-cyano-3,3-diphenylacrylate (INCI: octocrylene) and the 2-cyano-3,3-diphenyl-2-propenamide derivative is 2-cyano-3,3-diphenyl-2-propenamide [731-48-6].

Cyanoacetic acid esters are generally prepared using solid cyanoacetic acid in the presence of methanesulphonic acid as catalyst (as e.g. disclosed in U.S. Pat. No. 6,271,410). Surprisingly, it has now been found, that the cyanoacetic esters as defined above can also be prepared by using an aqueous solution of cyanoacetic comprising about 70 to 85 wt.-% of cyanoacetic acid while achieving the similar yields and quality, which from a cost viewpoint is highly preferable as such solutions are readily available. Furthermore, it has been found, that it is possible to use p-toluenesulfonic acid as catalyst which is less corrosive and cheaper.

Thus, in a further embodiment the invention relates to a process for the manufacture of substituted 2-cyanocinnamic esters according to the invention, wherein the cyanoacetic ester is prepared via a process comprising the reaction of a 70 to 85 wt.-% aqueous solution of cyanoacetic acid with a $C_1$-$C_{12}$ alcohol in the presence of a p-toluenesulfonic acid catalyst. Preferably no further solvents are used in the process. In a further embodiment, the molar ratio of cyanoacetic acid to the $C_1$-$C_{12}$ alcohol is selected within a range of about 0.5 to 0.8, in particular within a range of about 0.6 to 0.7. In another embodiment, the amount of the p-toluenesulfonic acid catalyst is additionally selected within concentration range of 0.2 to 0.3 mol % based on the cyanoacetic acid [mol]. In a particular embodiment, the molar ratio of cyanoacetic acid to the $C_1$-$C_{12}$ alcohol to the p-toluenesulfonic acid catalyst is in the range of about 1 to 1.5 to 0.0028.

In all embodiments of the invention, suitable $C_1$-$C_{12}$ alcohol are, for example, methanol, ethanol, propanol, isopropanol, butanol, isobutanol, pentanol, hexanol and 2-ethylhexanol, in particular 2-ethylhexylalcohol.

The term p-toluenesulfonic acid refers to pure p-toluenesulfonic acid as well as to the monohydrate.

In the process for the manufacture of cyanoacetic ester according to the invention the reaction temperature may vary from about 70° C. to 130° C. Preferably, the reaction temperature ranges from about 90° C. to 120° C., even more preferably from about 100° C. to 120° C. The reaction may be conducted above atmospheric pressure or under partial vacuum in order to achieve the desired temperature condition. The $C_1$-$C_{12}$ alcohol/water mixture can be distilled off at atmospheric pressure or at reduced pressure, for example from about 20 to 400 mbar e.g. using a Dean-Stark water separator. As soon as no more water separates out, the reaction can be regarded as being terminated. This is generally the case after from about 3 to 8 hours. The reaction product is worked up in a usual manner by separating the organic and the aqueous phase, optionally washed and finally distilled for further purification. The non converted starting materials such as the $C_1$-$C_{12}$ alcohol can be recycled by conventional methods such as via distillation or crystallization. Preferred processes according to the invention include the recycling of unreacted starting materials.

The following examples are provided to further illustrate the processes of the present invention. These examples are illustrative only and are not intended to limit the scope of the invention in any way.

EXAMPLE 1

Esterification of Cyanoacetic Acid

To a 1000 ml four neck flask fitted with mechanical agitator, thermometer, Dean and Stark apparatus and water condenser, add 237.5 g (2.23 mol on pure substance) 80 wt.-% cyanoacetic acid in water, 440 g (3.38 mol) 2-ethylhexanol and 1.2 g (6.3 mmol) p-toluenesulfonic acid monohydrate. Afterwards, the mixture is heated to reflux (110° C.) under atmospheric pressure for 1 hour and the water (both initial and formed) is azeotropically distilled out using a Dean and Stark apparatus returning the upper organic layer to the reactor. After 1 hour and at a temperature of 130° C. gradually a vacuum of 400 mbar is applied using a water respirator. The azeotropic distillation is maintained for further 6 hours while gradually increasing the vacuum from 400 mbar to 30 mbar in order to maintain a temperature of 130° C. until no further water is removed. After releasing the vacuum the reaction mixture is cooled to 90° C. After the addition of about 100 ml water (pre heated to 90° C.), the mixture is stirred at 85-90° C. for 10 minutes before separation of the phases. The upper organic layer is transferred to a 1000 ml four neck flask fitted with mechanical agitator, thermometer, packed column (ID=30 mm, H=1200 mm, packing metal raschid rings D=7 mm), water condenser and distillate flasks. Excess 2-Ethylhexanol is distilled out at 130-140° C. under a vacuum of 10-30 mbar. When complete increase the vacuum to 1.5 mbar and distilled out 2-ethylhexyl cyanoacetate at 130-140° C. 2-Ethylhexyl cyanoacetate is obtained as a colourless liquid. The reaction yield is 92% (based on cyanoacetic acid).

EXAMPLE 2

Determination of the Optimal Molar Ratio of 2-Ethylhexyl Cyanoacetate to Benzophenones Into a 500 ml four-neck round-bottom flask, equipped with a mechanical stirrer, a thermometer and a condenser is charged with 62.2 g (0.32 mmol) of 2-Ethylhexyl cyanoacetate (EHCA) and 81.0 g (0.45 mol) of Benzophenone (BP) (molar ratio EHCA:BP=0.71:1) and 27.7 g (0.36 mol) of ammonium acetate and 81.0 g (1.1 mol) of propionic acid and 81.0 g of heptane. The mixture is heated under stirring. When the temperature reach 110° C., a mixture of propionic acid, water, heptane is distilled off over a period of 5 hours at normal pressure. Heptane phase is returned back to the flask. Then the reactant is cooled to 90° C., and 100 ml of hot water is added to the reaction mixture. The mixture is kept at 85° C. for 10 minutes, and then transferred to a funnel for separation. To a flask equipped with a column 256.0 g of crude 2-ethylhexyl 2-cyano-3,3-diphenylacrylate solution is added. Rectification is carried out at 1 mbar. 2-Ethylhexyl 2-cyano-3,3-diphenylacrylate is distilled out at 210° C. (vapor). After distillation, light yellow 2-ethylhexyl 2-cyano-3,3-diphenylacrylate is obtained. Reaction yields are as indicated in table 1 and assume recycle of unreacted benzophenone and 2-EHCA.

The experiment is repeated by adjusting the amount of 2-EHCA in order to give the molar ratios as indicated in the table 1 below.

TABLE 1

| 2-EHCA:BP | 2:1 | 1:1 | 0.9:1 | 0.8:1 | 0.71:1 | 0.6:1 |
|---|---|---|---|---|---|---|
| Yield on 2-EHCA (%) | 66.18 | 85.60 | 88.24 | 90.34 | 93.09 | 84.41 |
| Yield on BP (%) | 94.02 | 94.05 | 94.28 | 95.30 | 98.38 | 88.30 |

As can be seen from the table, the optimal ratio of 2-EHCA to BP is in the range of about 0.7:1.

EXAMPLE 3

Determination of the Optimal Molar Ratio of Ammonium Compound to Benzophenone 20.6 g Methyl cyanoacetate (MCA) [0.2 mol], 182 g benzophenone (BP) [0.1 mol], 6.2 g ammonium acetate [0.08 mol], 40 g propionic acid and 40 g heptane are mixed and heated to 100° C. A mixture of water/heptane/propionic acid is distilled off over a period of 5 hours at normal pressure. Then, heptane and propionic acid are distilled out under 100~200 mbar vacuum. Most of unreacted MCA is distilled out at 130° C. under 50 mbar. The residue is cooled down, Methyl 2-cyano 3,3-diphenyl acrylate (MCDA) and part of unreacted BP is precipitated and filtrated. The solid is washed by 100 ml water for 2 times. Then crude MCDA is obtained and dried.

The experiment is repeated by adjusting the amount of the ammonium acetate catalyst in order to give the molar ratios catalyst:BP as indicated in the table 2.

TABLE 2

| catalyst:BP | 0.4 | 0.6 | 0.8 | 0.85 |
|---|---|---|---|---|
| BP conversion (%) | 80.07 | 73.15 | 75.56 | 77.24 |
| MCDA yield (%) | 28.05 | 92.42 | 95.28 | 92.4 |

EXAMPLE 4

Preparation of 2-Ethylhexyl 2-Cyano-3,3-Diphenylacrylate with a Low Content of 2-Cyano-3,3-Diphenyl-2-Propenamide A 2000 ml reactor is charged with 311 g of 2-ethylhexyl cyanoacetate, 70 g of ammoniumacetate, 404 g of benzophenones, 405 g of propionic acid and 405 g of n-heptane. The mixture is heated to about 95° C. under stirring at reduced pressure (about 700 mbar in order to maintain the reaction at reflux). When the temperature reached 95° C. a mixture of heptane, water and propionic acid is distilled off azeotropically over a period of 6 h wherein the organic phase is recharged back in the reactor. During this time every hour 25 g of additional ammonium acetate is added stepwise (5 portions, 1 per hour). After the reaction is finished heptane and propionic acid are distilled off at reduced vacuum (up to 20 mbar while keeping the temperature below about 95° C.). When no more distillate is observed, 500 g of water is added and the mixture is stirred for 10 min at 75° C. After adding 340 g of n-heptane the organic phase is collected and the washing procedure is repeated. After evaporation of the solvent at reduced pressure (temperature is maintained below 95° C.) the crude product (comprising about 0.04% of 2-cyano-3,3-diphenyl-2-propenamide) is collected followed by distillation using a wiped thin film evaporator. A second distillation yielded 388 g of light yellow octocrylene comprising about 0.38% of 2-cyano-3,3-diphenyl-2-propenamide (determined via HPLC). The reaction is repeated at normal pressure and a temperature of about 110° C. (reflux temperature) resulting after purification in an amount of 0.7% of 2-cyano-3,3-diphenyl-2-propenamide.

The invention claimed is:

1. A process for the manufacture of a compound of formula (I)

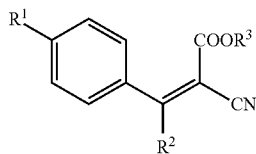

wherein
$R^1$ is hydrogen, $C_1$-$C_4$ alkyl groups, $C_1$-$C_4$ alkoxy group
$R^2$ is hydrogen, $C_1$-$C_4$ alkyl or phenyl and
$R^3$ is a $C_1$-$C_{12}$ alkyl, wherein
the process comprises reacting a cyanoacetic ester of formula (II) with a carbonyl compound of formula (III)

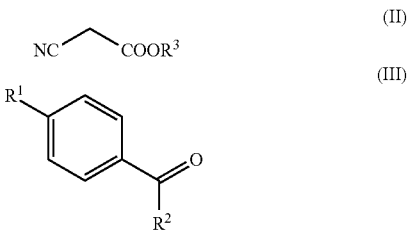

in a molar ratio of the cyanoacetic ester to the carbonyl compound in a range of about 0.7 to 0.8 and in the presence of:
(i) an organic solvent,
(ii) a $C_3$-$C_6$ monocarboxylic acid, and
(iii) an ammonium compound.

2. The process according to claim 1, wherein the organic solvent is an aliphatic solvent.

3. The process according to claim 1, wherein the organic solvent is selected from hexane, cyclohexane, heptane, isooctane, octane, methyl cyclohexane or mixtures thereof.

4. The process according to claim 1, wherein the organic solvent is heptane or cyclohexane or mixtures thereof.

5. The process according to claim 1, wherein the ammonium compound and the carbonyl compound are present in amounts to achieve a molar ratio of the ammonium compound to the carbonyl compound in a range of 0.6 to 1.5.

6. The process according to claim 1, wherein the $C_3$-$C_6$ monocarboxylic acid is propionic acid, butyric acid, isobutyric acid, valeric acid or isovaleric acid.

7. The process according to claim 1, wherein the ammonium compound is ammonium acetate or ammonium benzoate or an ammonium salt formed via addition of ammonia to the corresponding $C_3$-$C_6$ monocarboxylic acid used in the reaction.

8. The process according to claim 1, which comprises conducting the reaction at a reaction temperature in the range of 90 to 100° C. and a pressure sufficient to maintain the reaction at reflux.

9. The process according to claim 1, wherein the cyanoacetic ester is prepared via a process comprising reacting a 70 to 85 wt. % aqueous solution of cyanoacetic acid with a $C_1$-$C_{12}$ alcohol in the presence of a p-toluenesulfonic acid catalyst.

* * * * *